(12) United States Patent
Hashimoto et al.

(10) Patent No.: US 7,326,187 B2
(45) Date of Patent: Feb. 5, 2008

(54) FLUID CONTROL DEVICE

(75) Inventors: Satoru Hashimoto, Kyoto (JP); Ryoji Fujii, Hiroshima (JP); Kenji Sawa, Hiroshima (JP)

(73) Assignees: JMS Co., Ltd., Hiroshima-shi, Hiroshima (JP); Satoru Hashimoto, Kyoto-shi, Kyoto (JP)

( * ) Notice: Subject to any disclaimer, the term of this patent is extended or adjusted under 35 U.S.C. 154(b) by 0 days.

(21) Appl. No.: 10/524,607

(22) PCT Filed: Aug. 5, 2003

(86) PCT No.: PCT/JP03/09930

§ 371 (c)(1),
(2), (4) Date: Jul. 20, 2005

(87) PCT Pub. No.: WO2004/016314

PCT Pub. Date: Feb. 26, 2004

(65) Prior Publication Data

US 2006/0155248 A1    Jul. 13, 2006

(30) Foreign Application Priority Data

Aug. 13, 2002    (JP) ............................. 2002-235531

(51) Int. Cl.
*A61M 5/00* (2006.01)
(52) U.S. Cl. ...................... 604/246; 604/247
(58) Field of Classification Search ............... 604/246, 604/236, 247; 137/852
See application file for complete search history.

(56) References Cited

U.S. PATENT DOCUMENTS 3,710,942 A    1/1973 Rosenberg
5,624,395 A * 4/1997 Mikhail et al. .......... 604/99.04
5,727,594 A * 3/1998 Choksi ..................... 137/859
5,792,118 A * 8/1998 Kurth et al. ............. 604/246

(Continued)

FOREIGN PATENT DOCUMENTS

EP    0 419 880 A1    4/1991

(Continued)

*Primary Examiner*—Nicholas D. Lucchesi
*Assistant Examiner*—Laura Bouchelle
(74) *Attorney, Agent, or Firm*—Lowrie, Lando & Anastasi, LLP

(57) ABSTRACT

A fluid control device is characterized in that the device is structured of a hollow first fluid path (21) and second fluid path (22), a housing portion (1) formed between the first fluid path and the second fluid path and having a hollow portion with a cross-sectional area larger than cross-sectional areas of both fluid paths, and a valve member (3) that has a main body (31) and a projection portion (32) that are installed in an opening portion where the first fluid path is connected to the hollow portion and that is formed of an elastic material. The fluid control device enables the circulation of liquid when the pressure of liquid flowing from the first fluid path toward the second fluid path is more than a predetermined level. The fluid control device enables accurate and safe measurement of pressure including blood pressure, and, when flushing operation of an infusion circuit etc. is finished, the device enables speedy lowering of pressure to a value that accurately reflects blood pressure of a patient and enables obtaining of a necessary flow rate in a region where pressure is relatively low.

2 Claims, 5 Drawing Sheets

U.S. PATENT DOCUMENTS

| | | | |
|---|---|---|---|
| 6,231,539 B1 * | 5/2001 | Inoue et al. | 604/30 |
| 6,290,681 B1 * | 9/2001 | Brown | 604/246 |
| 2002/0002350 A1 * | 1/2002 | Larrain et al. | 604/247 |

FOREIGN PATENT DOCUMENTS

| | | |
|---|---|---|
| EP | 0 712 640 A1 | 5/1996 |
| JP | 54-48333 | 4/1979 |
| JP | 63-297878 | 12/1988 |
| JP | 01-171527 | 7/1989 |
| JP | 05-23308 | 2/1993 |
| JP | 6-39003 | 5/1994 |

* cited by examiner

FLUID CONTROL DEVICE

TECHNICAL FIELD

The present invention relates to a fluid control device for medical uses, particularly a fluid therapy; a valve structure of the fluid control device; and a blood pressure measurement system equipped with the fluid control device.

BACKGROUND ART

In a typical medical fluid therapy, a drug is administered into a blood vessel or the like of a patient via an infusion line from a container accommodating a drug, such as an infusion bag and an injector filled with a drug. In such a fluid therapy, there are cases in which the blood pressure of a patient is measured and monitored concurrently with drug administration as shown in FIG. 6. That is, a conventional infusion line consists of an injector 41 filled with a drug, a syringe pump 4 (a drug supplying part) for ejecting the drug from the injector 41, a tube member 7 for transporting the drug, and a puncture needle 9 provided at the end of the tube member and to be inserted into a blood vessel or the like of a patient for drug administration. Further, the infusion line is provided, at a midway point of the tube member 7, with a mixing/charging portion 8 which is adapted to enable blood sampling during treatment. The infusion line is also provided, in a line branched from a midway point of the tube member 7 and for supplying a drug solution to the patient's body, with a transducer 5 which is configured to convert the pressure in the infusion line into an electrical signal thereby providing an output to a pressure-value display means 6. Thus, a medical staff is allowed to constantly monitor the blood pressure of the patient by means of the pressure-value display means 6 while administering a drug. However, this type of blood pressure measuring systems had a drawback in that it was rather impossible, in practical use, to accurately monitor the pressure since the pressure in the tube member is affected by the pressure fluctuations of the syringe pump 4 upon administering a drug. This being the case, in order to overcome the drawback, there has been proposed an infusion line in which a flow control device is provided in midway of the line between the transducer 5 and the syringe pump 4. For example, in JP, A, 1-171527 or JP, A, 5-23308, there is proposed a flow control device having an entry path and an exit path, the entry path and the exit path being communicated through a communication path having a smaller cross section than those of the foregoing paths, characterized by being configured such that an elastic body is placed at the exit-path-side end portion of the communication path to close the exit-path-side end portion so that when the pressure of the fluid introduced from the entry path reaches a predetermined level, the elastic body is pressed to open the exit-path-side end portion and thus allowing the fluid to flow from the entry path to the exit path.

More particularly, the above described flow control device is comprised of: a first tubular member formed with the above described entry path thereinside and having a bulged portion at the tip end portion thereof; a second tubular member fitted to the first tubular member in such a way to surround the periphery of the bulged portion and defining the above described exit path in conjunction with the bulged portion; the above described communication path formed in the bulged portion; and a sealing member formed of an elastic material capped onto the bulged portion.

Further, as a flow control device, there is known a control device such as one used in the X line of the infusion line shown in FIG. 7. This flow control device used in the X line of FIG. 7 is configured to be integral with a transducer. The flow control device is provided with a path for flowing a fluid and a lever capable of changing the size of the path. This flow control device is to be used in such a way that the diameter of the path of the flow control device is significantly reduced for normal usage and the diameter of the path is increased upon a flushing operation thereby enlarging the path by controlling the lever.

Furthermore, in the above described infusion line, there is a case in which blood sampling for inspection is conducted from the mixing/charging portion 8 provided in the line during treatment. In such occasion, blood would remain in the tube member 7 between the patient and the mixing/charging portion 8 possibly leading to coagulation when left standing, and therefore it is necessary to return the blood to the patient side. This blood returning operation (generally called as a flushing operation) is performed by driving the syringe pump 4 to increase the flow rate of the drug thereby transporting the remaining blood to the patient. During this flushing operation, the pressure in the line is temporarily raised due to the actuation of the syringe pump 4 thus affecting pressure-value display means 6. Moreover, since the medical staff is supposed to be monitoring this pressure-value display means 6, the pressure-value needs to be reduced to a value accurately reflecting the patient's blood pressure soon after finishing the flushing operation. However, the flow control device described in each of the above mentioned patent publication had a problem in that it is difficult for a medical staff to accurately keep track of the blood pressure of a patient because it takes some time until a pressure rise in the line due to a flushing operation is eliminated. Moreover, the flow control devices disclosed in the above mentioned patent publications are configured such that a seal member having a tubular skirt is placed under a tension so as to come into intimate contact with the outer peripheral surface of the bulged portion, into which periphery the communication path opens, and this configuration makes it difficult to ensure a sufficient flow rate in a relatively low pressure range and to do so even at elevated pressures.

Further, the flow control device used in the X line of FIG. 7 is configured to change the diameter of the path through actuation of the lever, which significantly affects pressure readings of patient's blood pressure, thus raising concerns that there is too much burden on a patient such as infants, and besides it was difficult to obtain accurate pressure readings.

DISCLOSURE OF THE INVENTION

In view of the above described problems, the present invention relates to a fluid control device which makes it possible to perform more accurate and safer pressure measurement, to measure pressure values accurately reflecting the patient's blood pressure soon after finishing a flushing operation of the infusion line and so on, and to ensure a sufficient flow rate in a relatively low pressure range, and more particularly to a flow control device which can be opened by a predetermined fluid pressure and allows the fluid to flow exactly following the pressure applied to the fluid, in which the fluid flow according to the opening of the device will have substantially no effect on the fluid pressure on the side where the fluid is flown to (exit side), and which ensures a sufficient flow rate in a relatively low pressure range.

Accordingly, the present invention is addressed to provide a fluid control device, characterized by comprising: a first and a second fluid paths of a hollow shape; a housing portion formed between said first fluid path and said second fluid path and having a hollow portion with a cross sectional area larger than those of said both fluid paths; and a valve member mounted at an opening portion at which said first fluid path communicates with said hollow portion, having a body and a projection portion which satisfy below described requirements: (1) and (2), and being formed of an elastic material, wherein fluid flow is allowed above a predetermined fluid pressure of the fluid flowing from the first fluid path to said hollow portion, where:

(1) the body of said valve member is formed of a tubular member which can be inserted into said first fluid path, and has in its side portion at least one communication portion to allow fluid flow from the first fluid path to the hollow portion; and (2) said projection portion is formed at the tip end portion of said tubular member on the side of the hollow portion, and is configured to project towards the inner wall face of said housing portion and have on the inner side of the body a hollow cavity portion which communicates with said communication portion, wherein at least a part of the outer edge portion of said cavity portion sits on the inner wall face of said housing portion to close the fluid flow from the first fluid path to said hollow portion below a predetermined fluid pressure, but allows the foregoing fluid flow above a predetermined fluid pressure.

According to the above described configuration, the fluid supplied from the first fluid path 21 flows through a communication portion 313 which is formed of a concave portion 311 provided in the body portion 32 of the valve member 3 to reach the cavity portion 312. The valve member 3 is pressed toward the hollow portion 13 by the pressure of the fluid passed therethrough. At this moment, if the pressure has reached a predetermined pressure, the valve member 3 deforms towards the hollow portion 13, thus producing a gap between the edge portion of the projection portion 32 of the valve 3 and the hollow-portion base portion 133. This gap brings the first fluid path 21 and the hollow portion 13 into communication thereby allowing fluid flow. Further, if the pressure of the fluid from the first fluid path 21 is lowered, the edge portion 34 of the projection portion 32 and the hollow-portion base portion 133 will be brought into contact again due to the resilience of the valve member 3 itself thus closing the passage between the first fluid path 21 and the hollow portion 13. On the other hand, in the fluid control device of the present invention, the fluid will not flow to the side of the first fluid path even when the pressure of the fluid within the hollow portion 13 increases. That is, since the projection portion 32 is provided in the hollow portion 13 and the edge portion 34 of the projection portion 31 is in contact with the hollow-portion base portion 133, when the pressure inside the hollow portion 13 is raised, the projection portion 32 will be pressed at the same time thus increasing the force which keeps the edge portion 34 of the projection portion 31 and the hollow-portion base portion 133 in contact and further ensuring the sealing of the hollow portion 13 and the first fluid path 21.

The above described fluid control device can perform following functions: that is, when the pressure of the fluid flown from the first fluid path reaches a predetermined level, the valve member provided in the fluid control device will be pressed to form a communication portion, between the valve member and the housing wall face of the hollow portion, through which fluid flow is allowed from the first fluid path to the hollow portion, and even if the fluid pressure from the second fluid path is increased in the hollow portion, the valve member will not be opened by the pressure from the second fluid path side, which will eliminate any interference with the pressure in the tube member connected to the second fluid path, thus enabling accurate pressure measurement in the second fluid path; and further since the pressure of the fluid supplied by the drug supply device such as a syringe pump is dampened by the valve member fitted into the first fluid path, the effect on the pressure fluctuations of the fluid to be flown to the second fluid path side will be minimized.

Hereinafter, the configuration of the fluid control device of the present invention will be described in detail.

The fluid control device of the present invention is comprised of: for example as shown in FIG. 1, first fluid path 21 placed on the upstream side and connected to the fluid control device; second fluid path 22 on the downstream side; housing portion 1 located between the first and the second fluid paths and forming a hollow portion 13 with a cross sectional area larger than those of both the fluid paths; and valve member 3 which forms body portion 31 placed in the first fluid path and projection portion 32 projecting into hollow portion 13, and substantially closes the part of the first fluid path 21 communicating with the hollow portion 13 by means of the projection portion 32. As described above, the body portion 31 of the valve member 3 is placed in the first fluid path 21, because making the fluid flown from the first fluid path to flow through the communication portion 313 having a smaller cross sectional area is effective in dampening and thereby reducing the fluid pressure. Moreover, the projection portion 32 is placed to project toward the hollow portion because that is suitable for ensuring the directionality (unidirectional) of the fluid in the fluid control device. And, by this configuration, even if the fluid pressure in the hollow portion 13 is raised, the projection portion 32 will be pressed against the hollow-portion base portion 133 by the pressure, thus preventing the release of the contact between the edge portion 34 of the projection portion 32 and the hollow-portion base portion 133 ensuring sealing capability.

Since the above described projection portion 32 has its outer edge portion expanded toward the inner wall surface of the housing portion 1, the entire projection-portion edge portion 34 at which the opening portion is formed is also expanded thereby making it possible to ensure an enough flow rate the fluid passing through the communication portion.

The projection portion 32 of the valve member 3, which is placed at the location where the first fluid path 21 and the hollow portion 13 are communicated, is formed on its body-portion side with a hollow cavity portion 312, and thereby can be sufficiently and smoothly applied a fluid pressure to be transferred from the first fluid path 21 to the valve member 3 through the communication portion 313.

Moreover, the hollow portion 13 provided in the housing portion 1 has a cross sectional area larger than either of the cross sectional areas of the first and second fluid paths in order to effectively perform the operation for removing the air inside the line (priming operation). Furthermore, though the hollow portion 13 has an approximately cylindrical shape on its side communicating with the first fluid path 21, the hollow portion 13 preferably has, on its side communicating with the second fluid path, an approximately-circular cone shape of which diameter is successively reduced toward the second fluid path 22. With the shape of the hollow portion 13 on the side communicating with the second fluid path 22 being of an approximately-circular cone, there will be no stagnation point when the fluid is flown, and therefore no air or bubbles will be remained.

In view of the manufacturing process, since the first and the second fluid paths have small cross sectional areas, the assembly of the fluid control device of the present invention is preferably performed by placing, in advance, the valve member 3 in the first housing portion 11, and thereafter fitting the second housing portion 12 thereto.

The material used for the first housing portion 11 is preferably a soft material with higher flexibility or a material with larger thermal contraction compared with that for the second housing portion. This is because, in connecting tubular members, outwardly capping the tubular member with a higher flexibility onto the tubular member with a relatively higher hardness will result in a higher bonding strength between the both members. The material for the first housing portion 11 includes for example polypropylene resin, and the material for the second housing portion 12 includes for example polycarbonate resin; and particularly the combination of polypropylene as the material for the first housing portion 11 and polycarbonate for the second housing portion 12 is preferable since it will ensure the liquid tightness and pressure resistance of the housing portion 1. Moreover, usually such medical instruments are to be sterilized before usage. During such sterilization, the medical equipment will be subjected to a certain thermal load. Since, due to the thermal load, the material for the first housing portion for outward capping thermally contracts, the above described configuration, particularly when the material for the first housing portion has a higher flexibility than the material for the second housing portion, is advantageous for exploiting a heat treatment operation such as sterilization to attain a stronger bonding force.

As describe above, the fluid control device of the present invention enables a directional (unidirectional) control of fluid flow by means of the valve member; and also enables a free selection of the fluid pressure needed to open the valve member thereby allowing a fluid flow when flowing the fluid in one direction utilizing the directional (unidirectional) control. Further, opening of the valve member needed for a fluid flow can be achieved in a relatively low pressure range and, in addition, since relatively large opening for a fluid flow can be formed by the valve member, it is possible to ensure a sufficient flow rate in any opening pressure range including relatively low pressure ranges.

The above described fluid control device of the present invention is composed of a drug supply means, a transducer for measuring the pressure in a tubular member extending from the drug supply means, and a pressure-value display means for displaying the signals outputted from the transducer as a pressure value, and enables a precise pressure measurement, i.e. blood pressure measurement when used for a medical circuit, for example, an infusion line for measuring and monitoring the patient's blood pressure concurrently with drug administration.

The fluid control functions of the fluid control device of the present invention was tested by means of a drug supply line shown in FIG. 7 using an animal (dog) 83.

As shown in FIG. 7, one arterial pressure monitor line was divided into three branches, and one branch line (X line) was mounted with a heparin-added saline bag (constantly pressured at 300 mmHg) 80 and a flow control device 82 integrally configured with a transducer as described above (this flow control device was capable of adjusting the flow rate of the path by controlling a lever). The other two lines (Y and Z lines) were provided with a syringe pump 85, a flow control device of the present invention (Umbrella A) 86, and a transducer.

Further, although two lines: X and Y lines, were used in this test, the purpose of the test can be accomplished by either one of the lines.

The above described syringe pump 85 had a syringe size of 20 ml and fed fluid at a flow rate of 0.5 ml/h. The observation of the change in the waveform during blood returning was conducted by performing fast-forwarding of the syringe pump 85 on the lines Y and Z provided with Umbrella A 86 and by performing flushing on the line X provided with the flow control device 82, and the comparison of the blood pressure waveforms generated by the fast-forwarding of the syringe pump 85 and the flushing of the flow control device 82 was conducted by comparing each waveform displayed on Labview 84 while halting displayed images.

Further, the dampening effect of the pressure loaded for blood returning during a blood returning operation was tested using the fluid control device (Umbrella A) of the present invention in the above described drug supply line. The results of the test shows that the system using Umbrella A showed little changes of pressure during fast-forwarding for blood returning while the conventional method showed significant changes in the pressure by being directly affected by the pressurized bag.

From the test results described above, it is found that the system utilizing Umbrella A, which is the fluid control device of the present invention, is not only able to accurately measure the patient's blood pressure as shown in line 1 of FIG. 8, but also able to minimize the burden on the patient; thus the system is considered to be useful as the fluid control device particularly for infants.

BRIEF DESCRIPTION OF THE DRAWINGS

FIG. 1(A) is a longitudinal sectional view along the concave portion of the valve member provided in the fluid control device.

FIG. 1(B) is a longitudinal sectional view obtained by turning the section of FIG. 1(A) by 90 degrees.

In each of the above described drawings, each reference number denotes followings: 1 housing portion, 11 first housing portion, 111 fitting portion, 12 second housing portion, 121 fitting portion, 13 hollow portion, 131 cylindrical portion, 132 approximately-circular cone, 133 hollow-portion base portion, 21 first fluid path, 211 engaging portion, 22 second fluid path, 3 valve member, 31 body portion, 311 concave portion, 312 cavity portion, 313 communication portion, 32 projection portion, 33 engaging portion, 34 projection-portion edge portion, 4 syringe pump, 41 injector, 5 transducer, 6 pressure-value display means, 7 tube member, 8 mixing/charging part, 9 puncture needle, 10 fluid control device, 80 heparin-added saline bag, 82 flow control device configured to be integral with the transducer and for adjusting the flow rate of a fluid path by lever control, 83 animal (dog) used for the test, 84 Labview, 85 syringe pump, 86 fluid control device (Umbrella A) of the present invention, 87 transducer.

BEST MODE FOR CARRYING OUT THE INVENTION

1. Embodiment 1

Figure 1:
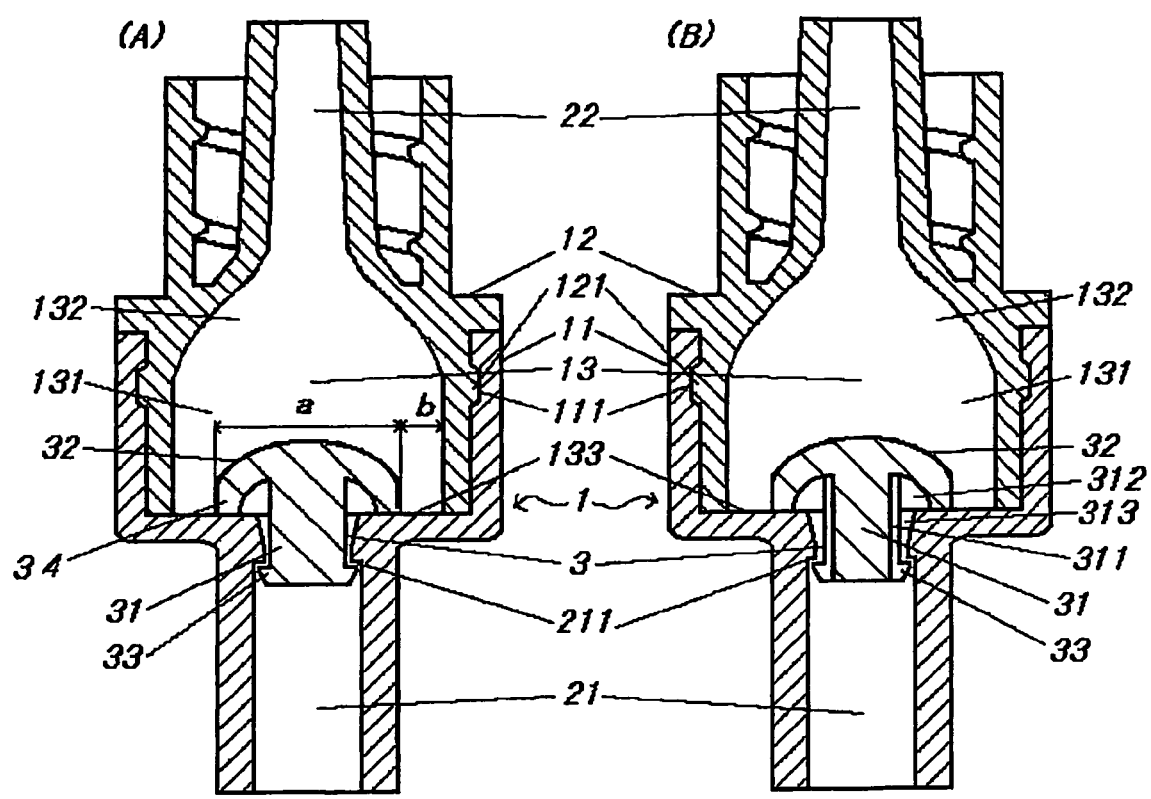
FIG. 1 is a longitudinal sectional view of the fluid control device of the present invention.
Figure 2:
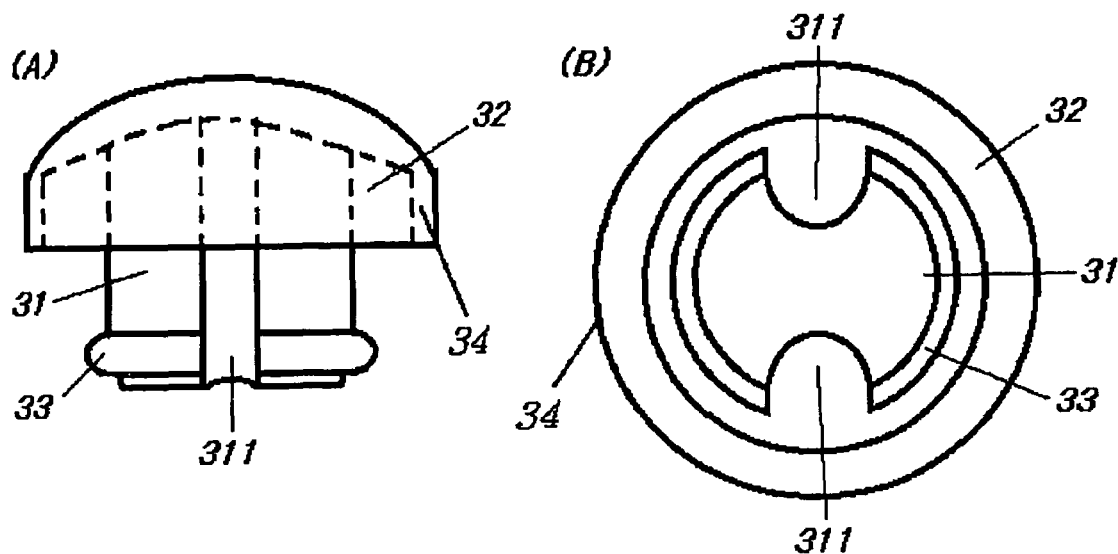
FIG. 2(A) is a front elevation view of the valve member of the fluid control device of the present invention.
FIG. 2(B) is a bottom view of the valve member viewed from the body side, wherein the valve member 3 is comprised of an approximately cylindrical body portion 31 and an approximately-hemispherical projection portion 32, and the valve member 3 as a whole exhibits an umbrella shape.

As shown in FIG. 1, the tube body constituting the first fluid path 21 is bulged at its end to form the first housing portion 11, and the tube body constituting the second fluid path is bulged at its end to form the second housing portion 12. The housing portion 1 is configured by fitting the second housing portion 12 into the first housing portion 11 so as to be enclosed therein, and the material for the first housing portion 11 is polypropylene resin and the material for the second housing portion 12 is polycarbonate resin.

Further, the first housing portion 11 and the second housing portion 12 are formed respectively with fitting portions 111, 121 having a convex and a concave shapes, and by engaging these fitting portions together, it is made possible to prevent both housing portions from being detached thereby ensuring air tightness and pressure resistance in the fluid control device.

The body portion 31 of the valve member 3 is formed of a cylindrical member inserted into the first fluid path, and the cylindrical member is provided, in its outer peripheral surface, with a concave portion 311 having an approximately semicircular shape at two opposing locations over the entire length of the body portion. Moreover, this concave portion 311 forms a communication portion 313 through which the fluid from the first fluid path 21 flows. The projection portion 32 of the valve member 3 is provided in its inside with a hollow cavity portion 312 communicating with the communication portion 313. In this embodiment, an embodiment in which the concave portion 311 is provided at two locations is shown; however, the present invention will not be limited only to this embodiment. For example, regardless whether the concave portion 311 is provided at one location or at more than two locations, the effect of the present invention will be fully achieved.

The fluid from the first fluid path 21 passes through the communication portion 313 to reach the cavity portion 312. The fluid pressure at this moment is applied to the cavity portion 312 and the projection portion 32 of the valve member 3 is pressed toward the hollow portion, and this pressing produces a gap between the edge portion 34 of the projection portion 32, which are contacted at the opening portion of the first fluid path on the side of the hollow portion 32 ensuring the sealing thereof, and the hollow-portion base portion 133, thereby forming an opening portion to allow the fluid to flow to the hollow-portion side.

The valve member is formed on its body-portion side with a cavity portion 312 having a hollow, approximately-hemispherical shape, which increases the area on which the fluid pressure transferred from the first fluid path 21 to the valve member 3 via the communication portion 313 is applied, and makes it possible to smoothly guide the fluid introduced into the communication portion to the opening portion through which the fluid flows.

The length (b in FIG. 1) between the edge portion of the projection portion, which is provided at the location where the first fluid path 21 communicates with the hollow portion 13, and the inner wall surface of the housing portion 1 is preferably between 1.5 mm to 5 mm. This is because, when the aforementioned length is below 1.5 mm, the volume inside the hollow portion 13 becomes too small making it difficult to effectively remove air or bubbles in performing the operation of removing the air in the line by filling a drug (priming operation), which is to be performed before using the infusion line which utilizes the fluid control device of the present invention. On the contrary, when the length b is above 5 mm, the volume of the hollow portion 13 becomes too large, not only making the entire device bulky but also increasing unnecessary priming volume.

Further, since the valve member 3 of this embodiment is configured such that its edge portion 34 sits on the hollow-portion base portion 133 of the bulged portion constituting the first fluid path, the sealing against the fluid flow between the first fluid path 21 and the hollow portion 13 is ensured below a predetermined fluid pressure.

Furthermore, the projection portion 32 of the valve member 3 has an approximately-hemispherical shape having an arcuate part facing the side of the second fluid path, which makes it possible to smoothly and sufficiently guide the fluid flowing from the first fluid path toward the second fluid path through the hollow portion to the vicinity of the opening portion through which the aforementioned fluid passes.

The functions of the valve 3 so far described make it possible to achieve an open/close control mechanism which can open or close exactly following the predetermined fluid pressure applied, and also allows fluid flow even by a low fluid-pressure transferred from the first fluid path 21.

The valve member 3 is formed, in its end portion opposite to the projection portion 32 of the body portion 31, with an engaging portion 33, and also the first fluid path 21 is provided in its inside with an engaging portion 211 which is engageable with the aforementioned engaging portion 33.

By engaging both aforementioned engaging portions, it is not only made possible to mount the valve member 3 to the housing 1 with the prevention of easy detachment, but also made possible to adjust the force level for contact the valve member 3 to the hollow-portion base portion 133 by utilizing the engagement structure, thereby ensuring the sealing ability of the valve member 3 against fluid flow.

Figure 3:
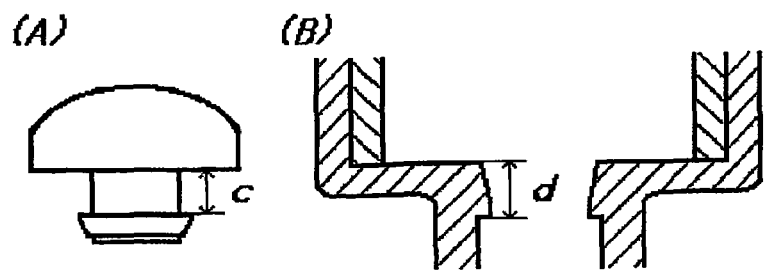
FIG. 3(A) is an enlarged elevation view of the valve member of the fluid control device of the present invention.
FIG. 3(B) is an enlarged sectional view of the first housing portion.

That is, as shown in FIG. 3, the length (c) of the body portion 31 and the length (d) from the engaging portion of the first fluid path 21 to the hollow-portion base portion 133 are configured to be (c)<(d), and by satisfying this requirement of (c)<(d), the force for contact the valve member 3 to the hollow-portion base portion 133 is applied and thereby the valve member 3 is placed under a tension in the lengthwise direction of the first housing portion 11 ensuring a more reliable sealing.

The relationship between the length (c) and length (d) is selectable as appropriate depending on applications for following reasons. For example, when the difference between length (c) and length (d) is small, although the force for cotact the valve member 3 is reduced, the pressure needed to form an opening portion between the valve member 3 and the hollow-portion base portion 133 is lowered. On the contrary, when the difference between length (c) and length (d) is large, although the force for contact the valve member 3 becomes strong, the pressure needed to form an opening portion between the valve member 3 and the hollow-portion base portion 133 will become higher.

Particularly, the relationship between length (c) and length (d) is preferably such that (c):(d) is from 1:1 to 1:1.25, or (c) is 1.45 mm and (d) is from 1.45 to 1.8 mm. Any configuration which satisfies such requirements can provide a fluid control device which allows a fluid flow from the first fluid path to the second fluid path in a low pressure range such as a fluid pressure of below 0.2 Kgf/cm$^2$ while exhibiting an dampening effect so as not to affect the pressure of the second fluid path.

The valve member 3 is preferably formed of an elastic member: for example, various rubber materials such as natural rubber, isoprene rubber, butadiene rubber, styrene-butadiene rubber, nitrile rubber, chloroprene rubber, butyl rubber, acryl rubber, ethylene-propylene rubber, hydrin rubber, urethane rubber, silicone rubber, silicon rubber, fluoro rubber; and various thermoplastic elastomers such as, styrene system, polyolefin system, polyvinyl chloride system, polyurethane system, polyester system, polyamide system, polybutadiene system, trans-polyisoprene system, fluoro rubber system, and chloric polyethylene system.

Particularly, the valve member 3 is preferably formed of silicon rubber. That is because silicon rubber has an elastic force and can provide a sufficient elastic force needed for the valve member, and also because silicon rubber has an excellent drug resistance.

In medical instruments, use of organic solvents such as adhesives may pose the risk that they may elute into drugs making it impossible to ensure safety, and therefore is not preferable. However, the fluid control device of this embodiment is constructed through the fitting of the first housing member 11 and the second housing member 12 without using adhesives; therefore it is a preferable fluid control device in the viewpoint of avoiding the use of adhesives.

2. Embodiment 2

Figure 4:
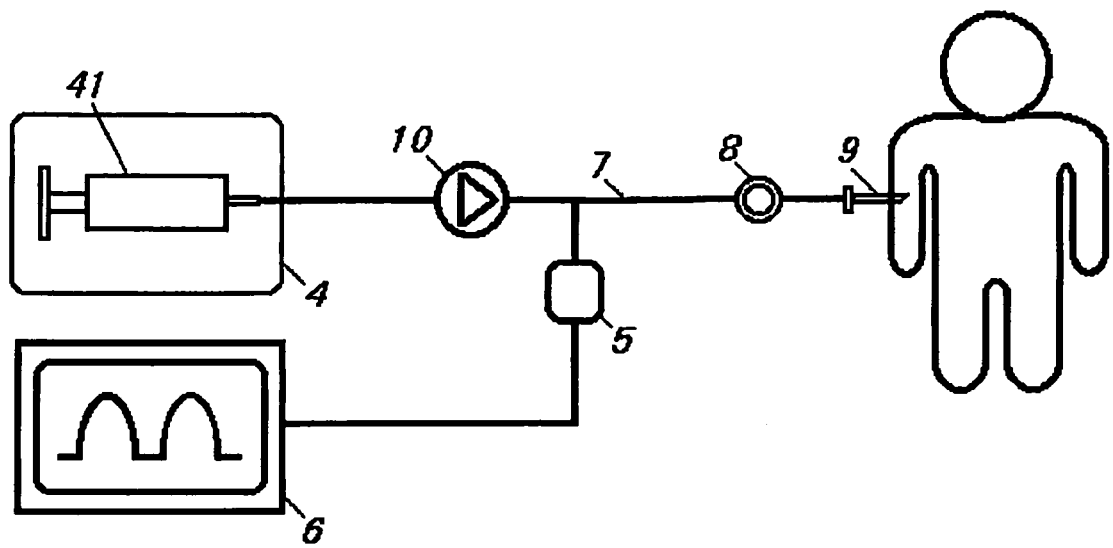
FIG. 4 is a schematic view of a blood pressure measuring system installed with the fluid control device of the present invention.

FIG. 4 is a schematic view of a blood pressure measurement system installed with the fluid control device of the present invention and for conducting blood pressure measurement while performing an infusion therapy, in which providing the fluid control device of the present invention in the infusion therapy line as described below makes it is possible: to prevent pressure fluctuations in the line due to the installment of the fluid control device, to accurately detect the pressure of the fluid flowing in the line, to complete a flushing operation in a shorter period of time, and further to readily cope with any alarm setting level of the alarm device provided in the line.

A patient is administered with a drug, which is delivered from the injector 41 through the driving of the syringe pump 4 into the blood vessel or the like via the tube member 7 and the puncture needle provided at the tip end thereof. At this moment, there is provided a line branched from a midway point of the tube member 7, and a transducer 5 is placed in the foregoing line to measure the pressure of the fluid. The pressure signal detected by the transducer 5 is visualized as a waveform of the pressure value by means of a pressure-value display device 6 thereby allowing monitoring by a medical staff. The fluid control device 10 is placed in the upstream side (with respect to the syringe pump 4) of the line. Providing this fluid control device 10 enables more accurate pressure measurements. That is because the fluid control device 10 can attenuate the pressure rise caused by a drug supply device such as a syringe pump positioned in the upstream of the line and therefore has substantially no effect on the pressure of the fluid in the downstream (the side of the line where the transducer 5 is provided). Further, since the fluid control device 10 has a characteristic of allowing the fluid to flow only in one direction, the fluid pressure in the line provided with the fluid control device 10 will have no interference from the fluid control device, thereby producing no pressure fluctuations.

Figure 5:
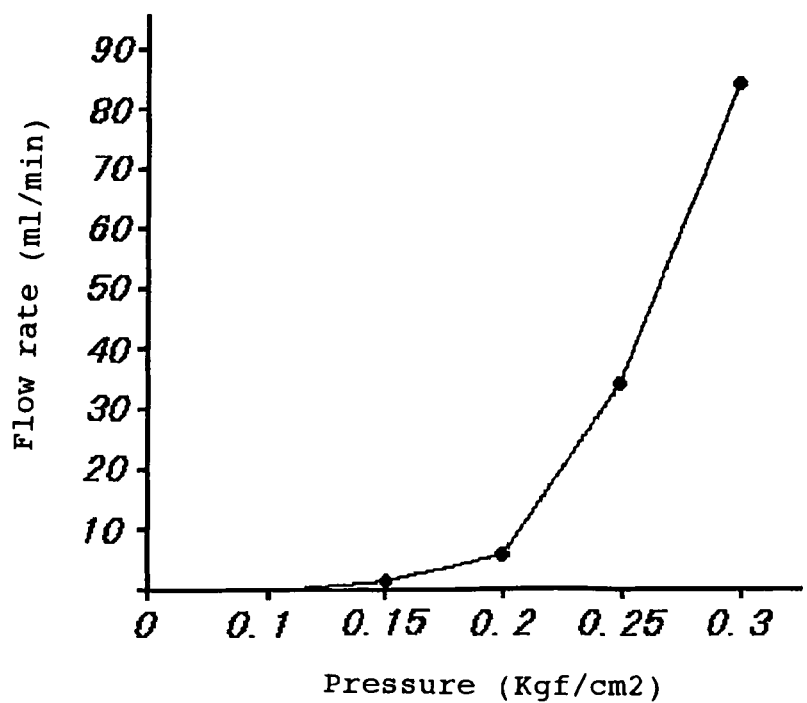
FIG. 5 is a graph to show the change of flow rate due to the pressure load in the fluid control device of the present invention.
Figure 6:
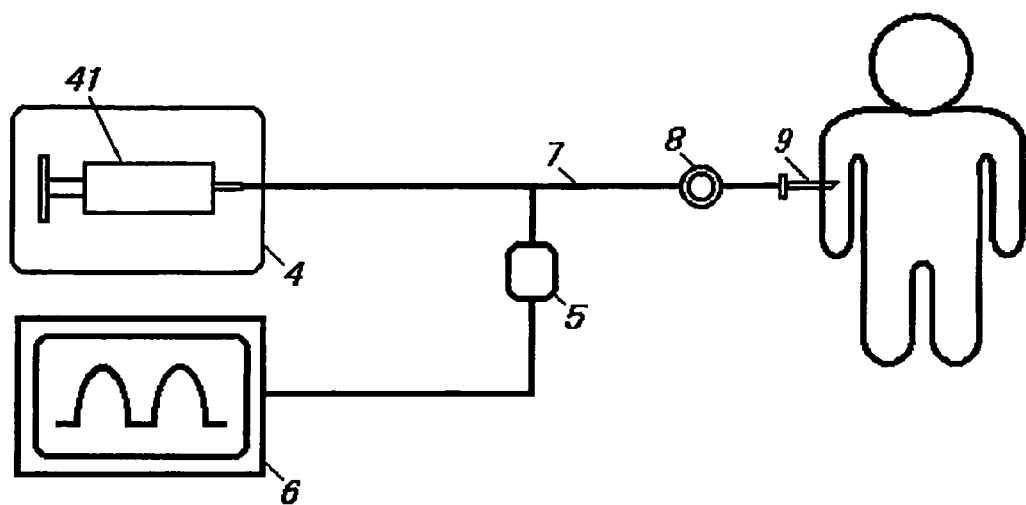
FIG. 6 is a schematic view of a conventional blood pressure measuring system.
Figure 7:
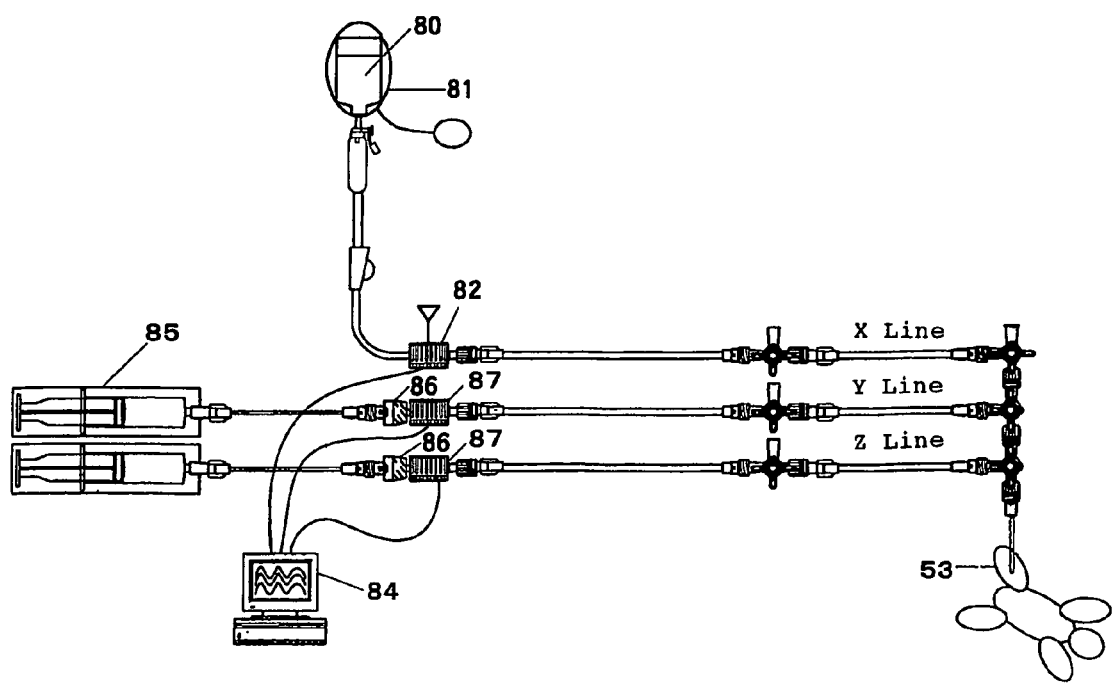
FIG. 7 shows a drug solution supply line used for the test of the fluid control functions of the fluid control device of the present invention.
Figure 8:
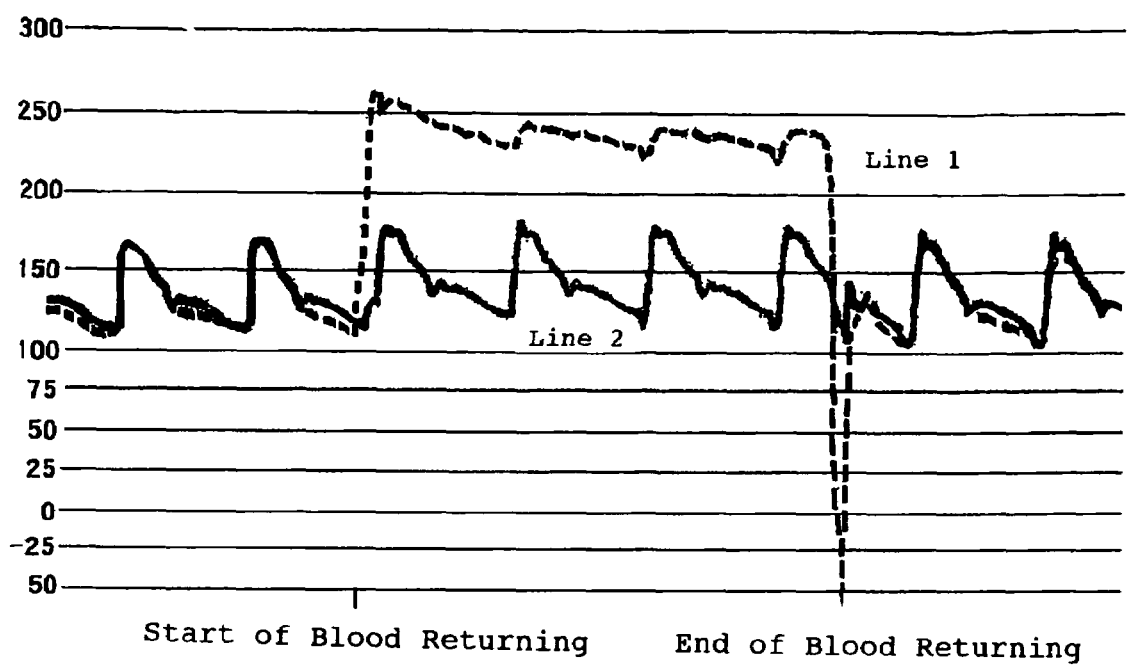
FIG. 8 shows test results of the fluid control functions by use of the drug solution supply line of FIG. 7.

On the other hand, there is a case in which blood sampling for inspection is performed from the mixing/charging portion 8 provided in the line during treatment. At this time, since the blood would remain in the tube member 7 between the puncture needle 9 and the mixing/charging portion 8 possibly leading to coagulation when left standing, it is necessary to return the blood to the patient's side. This blood returning operation (generally called as a flushing operation) is performed by driving the syringe pump 4 so as to produce a higher flow speed (fast-forwarding operation) thereby transporting the remaining blood to the patient. Typically, the fast-forwarding operation of the syringe pump 4 is performed under a pressure load of 0.3 Kgf/cm$^2$ and, in this respect, the fluid control device 10 is advantageous because it can ensure a larger flow rate and therefore can complete the flushing operation within a shorter period of time. That is, FIG. 5 is a graph to show the change in the flow rate with respect to the pressure load in the fluid control device of the present invention, indicating that at a pressure of 0.3 Kgf/cm$^2$ produced by the fast-forwarding operation of the syringe pump 4, the fluid control device of the present invention can ensure a flow rate of not less than 80 ml/min. Although the fluid pressure on the downstream side will be raised slightly when a flushing operation is performed keeping such a flow rate; by reducing the pressure produced by the fast-forwarding of the syringe pump 4 to the pressure for normal usage after completing the flushing operation, the fluid control device of the present invention can rapidly reduce the flow rate following the fluid pressure and therefore have little effect on the pressure fluctuations on the downstream side. Further, due to the advantage that flushing operation can be completed in a shorter time period, the duration of pressure rise in the downstream will also be reduced, which is very advantageous for a medical staff to perform accurate pressure monitoring.

For normal usage, the syringe pump 4 has, as sensing means for a closure of the path, an alarming mechanism for issuing an alarm when a predetermined pressure is reached. Generally, the setting of the pressure sensed by the syringe pump is variable, and the minimum value of the alarm setting level of the syringe pump during normal usage is around 0.2 Kgf/cm$^2$; therefore, when the opening pressure of a fluid control device exceeds 0.2 Kgf/cm$^2$, an alarm will be issued and which is undesirable.

However, even in a case in which the alarm setting pressure needs to be set at a low pressure (opening pressure) below about 0.2 Kgf/cm$^2$, by using a fluid control device with a low pressure (opening pressure) below about 0.2 Kgf/cm$^2$, the valve member of the fluid control device will be opened before alarm is issued, allowing the flow of a sufficient amount of the fluid. Thus, it is made possible to flow a sufficient amount of the fluid without an alarm being issued and also made possible to detect whether an abnormal condition has occurred or not by means of the mechanism for issuing an alarm, which is effective in performing a safe therapy (an infusion therapy in this embodiment). However, the opening pressure of the fluid control device of the present invention may be higher or lower than 0.2 Kgf/cm$^2$ and, for example, 0.1 to 0.5 Kgf/cm$^2$ may be mentioned.

Further, in the case of this embodiment, an infusion therapy has been described as a preferable aspect, the fluid control device of the present invention will be similarly effective in other types of therapy lines.

INDUSTRIAL APPLICABILITY

The fluid control device of the present invention can be opened at a predetermined pressure to allow a fluid flow, and the pressure of the fluid needed to effect opening can be set with relative ease. Further the fluid control device of the present invention can ensure a sufficient flow rate even when the applied pressure is relatively low, and can flow the fluid accurately following the applied pressure, thereby enabling flow rate control in a relatively low pressure range, and thus the fluid flow associated with the opening of the device substantially have no effect on the fluid pressure of the side where the fluid is flown to (exit side). The fluid control device of the present invention can provide a fluid control device which enables more accurate and safer pressure measurement, or a blood pressure measurement system which utilizes the present fluid control device.

The invention claimed is:

1. A fluid control device, comprising:

a first fluid path and a second fluid path each having a hollow shape;

a housing portion formed between said first fluid path and said second fluid path and having a hollow portion with a cross sectional area larger than those of said first and second fluid paths; and a valve member mounted at an opening portion at which said first fluid path communicates with said hollow portion, the valve member having a body and a projection portions, wherein the body of said valve member is formed of a tubular member which can be inserted into said first fluid path, the tubular member including a side portion having at least one communication portion to allow fluid flow from the first fluid path to the hollow portion, the communication portion of the valve member body portion being a concave portion formed in the side portion of the valve member body portion, wherein said projection portion is formed at a tip end portion of said tubular member on a side of the hollow portion, and is configured to project towards an inner wall face of said housing portion and have on an inner side of the body a hollow cavity portion which communicates with said communication portion, wherein at least a part of an outer edge portion of said hollow cavity portion sits on the inner wall face of said housing portion to close the fluid flow from the first fluid path to said hollow portion below a predetermined fluid pressure, but allows the fluid flow above a predetermined fluid pressure in such a way that the outer edge portion sitting on the inner wall face of said housing portion is deformed by the fluid pressure towards the hollow portion, thus producing a gap between the edge portion and a base of the hollow portion, wherein the housing portion is comprised of a first housing member formed by bulging an end of the first fluid path and a second housing member formed by bulging an end of the second fluid path, and is formed through a fitting of said two housing members without using adhesives, and wherein the material of the first housing member has a larger thermal contraction compared to the material of the second housing member.

2. A fluid control device, comprising:

a first fluid path and a second fluid path each having a hollow shape;

a housing portion formed between said first fluid path and said second fluid path and having a hollow portion with a cross sectional area larger than those of said first and second fluid paths; and a valve member mounted at an opening portion at which said first fluid path communicates with said hollow portion, the valve member having a body and a projection portions, wherein the body of said valve member is formed of a tubular member which can be inserted into said first fluid path, the tubular member including a side portion having at least one communication portion to allow fluid flow from the first fluid path to the hollow portion, the communication portion of the valve member body portion being a concave portion formed in the side portion of the valve member body portion, wherein said projection portion is formed at a tip end portion of said tubular member on a side of the hollow portion, and is configured to project towards an inner wall face of said housing portion and have on an inner side of the body a hollow cavity portion which communicates with said communication portion, wherein at least a part of an outer edge portion of said hollow cavity portion sits on the inner wall face of said housing portion to close the fluid flow from the first fluid path to said hollow portion below a predetermined fluid pressure, but allows the fluid flow above a predetermined fluid pressure in such a way that the outer edge portion sitting on the inner wall face of said housing portion is deformed by the fluid pressure towards the hollow portion, thus producing a gap between the edge portion and a base of the hollow portion, wherein the housing portion is comprised of a first housing member formed by bulging an end of the first fluid path and a second housing member formed by bulging an end of the second fluid path, and is formed through a fitting of said two housing members without using adhesives, and wherein the material of the first housing member is polypropylene resin and the material of the second housing member is polycarbonate resin.

* * * * *